United States Patent [19]

Schaefer

[11] 3,959,770
[45] May 25, 1976

[54] METHOD AND APPARATUS FOR ERROR COMPENSATION IN MULTICHANNEL SYSTEMS

[75] Inventor: Louis F. Schaefer, Palo Alto, Calif.

[73] Assignee: Stanford Research Institute, Menlo Park, Calif.

[22] Filed: Oct. 21, 1974

[21] Appl. No.: 516,674

[52] U.S. Cl. .................... 340/146.1 E; 179/15 AE; 325/41; 340/5 MP
[51] Int. Cl.² ......................................... H04B 1/62
[58] Field of Search ......... 340/5 MP, 5 H, 15.5 GC, 340/146.1 E; 179/15 AE; 325/41

[56] References Cited
UNITED STATES PATENTS

| | | | |
|---|---|---|---|
| 3,150,327 | 9/1964 | Taylor | 340/15.5 GC |
| 3,691,517 | 9/1972 | Riggs | 340/5 H |
| 3,831,135 | 8/1974 | Smith | 340/5 MP |

Primary Examiner—Maynard R. Wilbur
Assistant Examiner—T. M. Blum
Attorney, Agent, or Firm—Victor R. Beckman

[57] ABSTRACT

Error compensating method and means are shown for use in multichannel systems for compensation of errors in the operating characteristics of the individual information handling channels. Offset, gain, linearity and the like, channel transfer function errors, may be compensated for in accordance with the invention. Error compensating signals for the individual information handling channels are stored in error compensating signal storage means and are combined with the channel output signals to compensate for errors therein. A test signal is supplied to the channel inputs, and the compensated channel outputs resultant thereof are compared with a standard related to said test signal. Variations from the standard are used to update the error compensating signals contained in storage.

15 Claims, 7 Drawing Figures

METHOD AND APPARATUS FOR ERROR COMPENSATION IN MULTICHANNEL SYSTEMS

BACKGROUND OF INVENTION

The invention described herein was made in the course of work under a grant or award from the Department of Health, Education and Welfare.

Many systems include a plurality of information handling channels of identical design such that with identical design such that with identical channel inputs the channel outputs also should be identical. Differences in outputs under identical input conditions often occur, however, and such differences may be due to different channel gains, noise figures, d.c. output levels and the like. To minimize distortion it has been the practice to suspend normal operation and then test and adjust the individual channels to compensate for various operating errors.

SUMMARY OF INVENTION

An object of this invention is the provision of an improved multichannel method and system in which various operating errors in the individual channels may be automatically compensated for during operation for improved system operation.

An object of this invention is the provision of improved error compensating method and means for use with systems which include a plurality of information handling channels of the same design, which compensate for variations in operating characteristics of the individual channels.

The above and other objects and advantages of the invention are achieved, in brief, by providing a store of error compensating signals which are combined with the channel output signals to compensate for errors therein. With minimum disruption of normal operation, the error compensating signals are updated by supplying test signals to the individual channel inputs and sensing variations in the resultant outputs from the error compensated channels, which variations are used to control the updating process.

BRIEF DESCRIPTION OF DRAWINGS

In the drawings, wherein like reference characters refer to the same parts in the several views.

DESCRIPTION OF PREFERRED EMBODIMENTS

Figure 1:
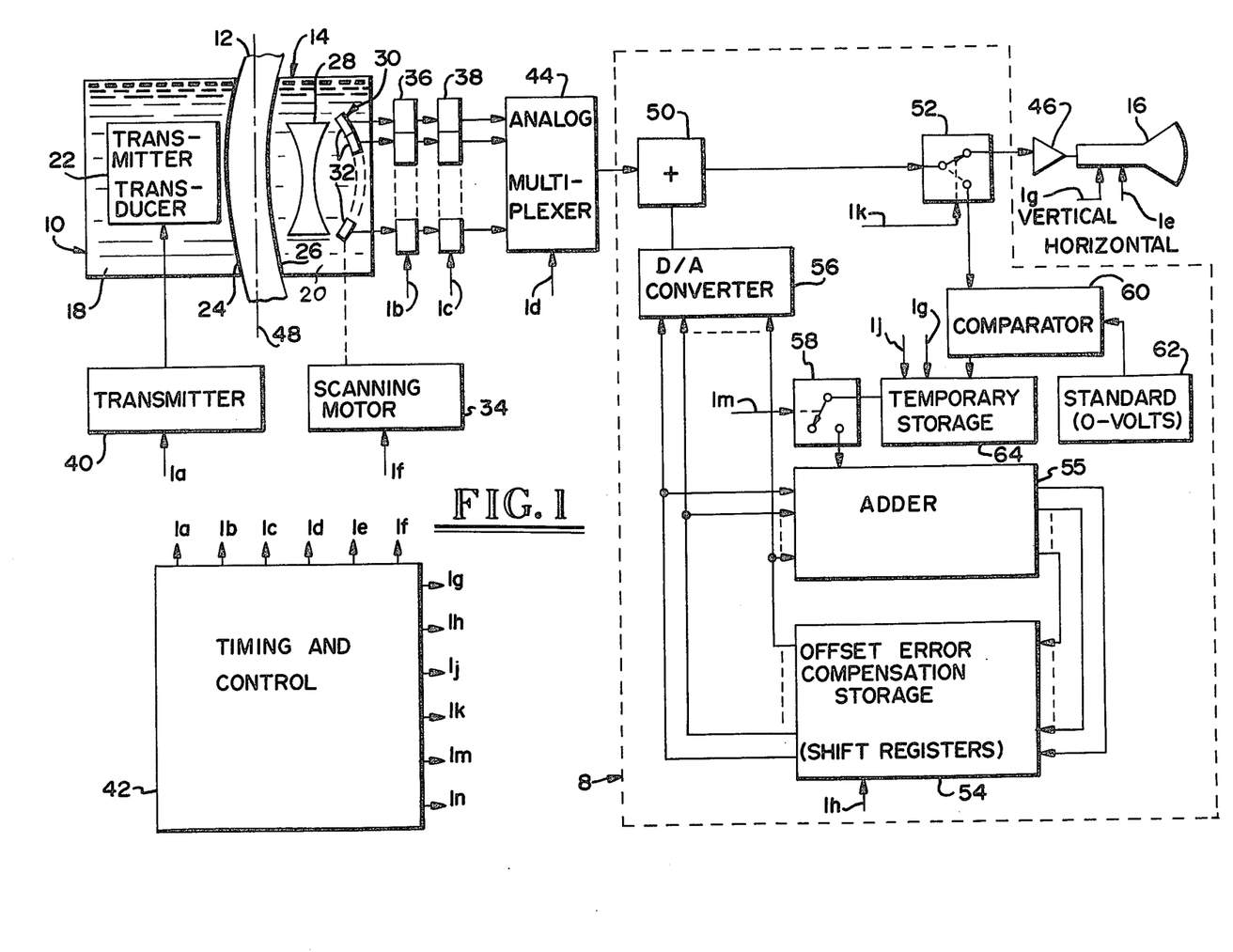
FIG. 1 is a block diagram illustrating an embodiment of the invention providing for offset error compensation of channel outputs from an ultrasonic camera.

Reference first is made to FIG. 1 wherein there is shown one form of error compensation means 8 which embodies this invention and which is shown for purposes of illustration as employed in a prior art acoustic camera system. The illustrated acoustic camera system includes a plurality of information handling channels which ideally have identical operating characteristics for proper system operation. The system, shown in simplified block diagram form, includes an acoustic transmitting unit 10 used to insonify a subject 12 and an acoustic camera or receiving unit 14 which receives and focuses the compressional wavefield from the insonified subject and translates said wavefield into electrical signals which are converted into a real time visual display of the insonified subject at the face of a cathode ray tube 16.

Both the transmitting and receiving units 10 and 14 are filled with a suitable acoustic transmission medium 18 and 20, such as water, for the support of acoustic waves produced by the acoustic wave generating transducer 22 included in the transmitting unit 10. Ultrasonic compressional waves generated by the transducer 22 are transmitted through the medium 18 and are coupled through an acoustically transparent window 24 to the subject 12 to insonify the same. The wavefield from the subject 12 is coupled through a liquid tight acoustically transparent window 26 at the receiving unit to the liquid 20 therewithin. An acoustic lens, or lens assembly, 28 is located within the liquid medium to focus the acoustic waves from the insonified subject onto acoustic receiver transducer means 30. The illustrated transducer 30 comprises a linear array of piezoelectric elements 32 individually responsive to the instantaneous field pressure thereat. For purposes of description only, an array which includes 192 such piezoelectric elements is shown. Preferably, the array is arranged in an arc, as viewed from above in FIG. 1, to better fit a single line across the compressional acoustic image field focused thereon by the lens 28. Also, the lens 28 may be longitudinally movable within the receiver unit for focusing at any desired level within the body 12 under investigation.

To obtain a two dimensional display of the insonified subject 12 the compressional acoustic image field and receiving array are periodically relatively moved up and down to relatively sweep the wave and array. In the illustrated arrangement the array 30 is periodically moved up and down by the use of a scanning drive motor 34. Alternatively, the acoustic wave from the lens may be periodically deflected to sweep the wave over the receiving array. A composite acoustic lens assembly for both focusing and periodically deflecting the waves which could be employed herein is shown in copending patent application Ser. No. 411,729, filed Nov. 1, 1973, but for simplicity of description a mechanically scanned receiver array is shown.

The electrical signals generated by the piezoelectric elements 32 are supplied to receivers 36 and thence to sample and hold circuits 38. With an array of 192 piezoelectric elements there are required 192 receivers and 192 sample and hold circuits, respectively, of identical design. The receivers may each comprise a preamplifier, a variable gain amplifier having an output which is fed to a filter tuned to the frequency of the ultrasonic wave, a signal detector, and low pass filter for removal of the high frequency components of the detected signal. The receiver outputs, therefore, comprise analog signals dependent upon the level of the high frequency signals obtained from the piezoelectric elements 32. Operation of the receiver amplifiers in either linear or nonlinear modes is contemplated.

Single, plural or frequency modulated sonic waves may be used which, typically, are within the range of, say, 1 to 10 MHz. A transmitter 40 comprising a gated oscillator tuned to the desired frequency, or comprising a frequency modulated signal source, has an output which is supplied to the transmitting transducer 22. The transmitter is recurrently gated on under control of a signal 1A (FIG. 2) supplied thereto over line or circuit 1a from a timing and control unit 42.

In the pulse mode operation exemplified in the drawings the transmitter transducer 22 is recurrently energized to generate pulses of ultrasonic waves for insonifying the subject or object 12. After a time delay dependent upon the transit time of the acoustic wave in traveling between transmitting transducer 22 and receiving array 30, the receivers 36 are turned on under control of a receiver gate control signal 1B (FIG. 2) supplied thereto from the timing and control unit 42 over circuit 1b. After stabilization of the receiver operation, sample and hold circuits 38 are simultaneously switched to the sample mode for simultaneous sampling of all of the receiver outputs, the control signal 1C for the sample and hold circuits being supplied thereto over control line 1c from the timing and control unit 42. The simultaneous sampling is taken over a short time period, at the end of which period the sample and hold circuits are switched back to the hold mode for subsequent conversion of the stored information therein into a composite video signal for input to the cathode ray tube 16. After the sampling operation the receivers may be turned off under control of the circuit 1b signal.

A composite video information signal is provided by sequentially reading out, or scanning, the information stored in the sample and hold circuits by means of an analog multiplexer, or scanner, 44 under control of signals 1D supplied thereto over circuit 1d from the timing and control unit 42. The signal at the multiplexer output passes through the error compensating means 8 of this invention for offset error compensation, in a manner described below, and thence through a video amplifier 46 to the control grid of the cathode ray tube 16 for density control of the electron beam directed onto the face, or screen, of the tube. Simultaneously, during the multiplexing operation, a horizontal sweep signal 1E is applied to the horizontal deflection circuit of the cathode ray tube through circuit 1e from the timing and control unit 42 for production of a scan line across the tube screen as the composite video signal is supplied to the control grid of the tube.

As noted above, in the illustrated arrangement the receiving transducer array 30 is moved up and down vertically (in a direction in and out of the plane of the drawing FIG. 1) to periodically sweep the line of acoustic receiving transducer elements 30 across the compressional image field. The scanning motor 34 for movement of the receiving array is under control of a signal 1F from the timing and control unit 42 supplied thereto over line 1f. Simultaneously the vertical deflection circuit of the cathode ray tube 16 is supplied with deflection voltage 1G over circuit 1g for simultaneous scanning of the receiver array 30 and the cathode ray tube beam in the vertical direction. Successive horizontal scans produced during successive analog multiplexer 44 scanning operations are thereby vertically deflected by the slow vertical scan to provide a two dimensional, real time, sectional image of the subject 12, along the object plane 48, on the face of the cathode ray tube as the above described cycle of operation is repeated.

Figure 2:
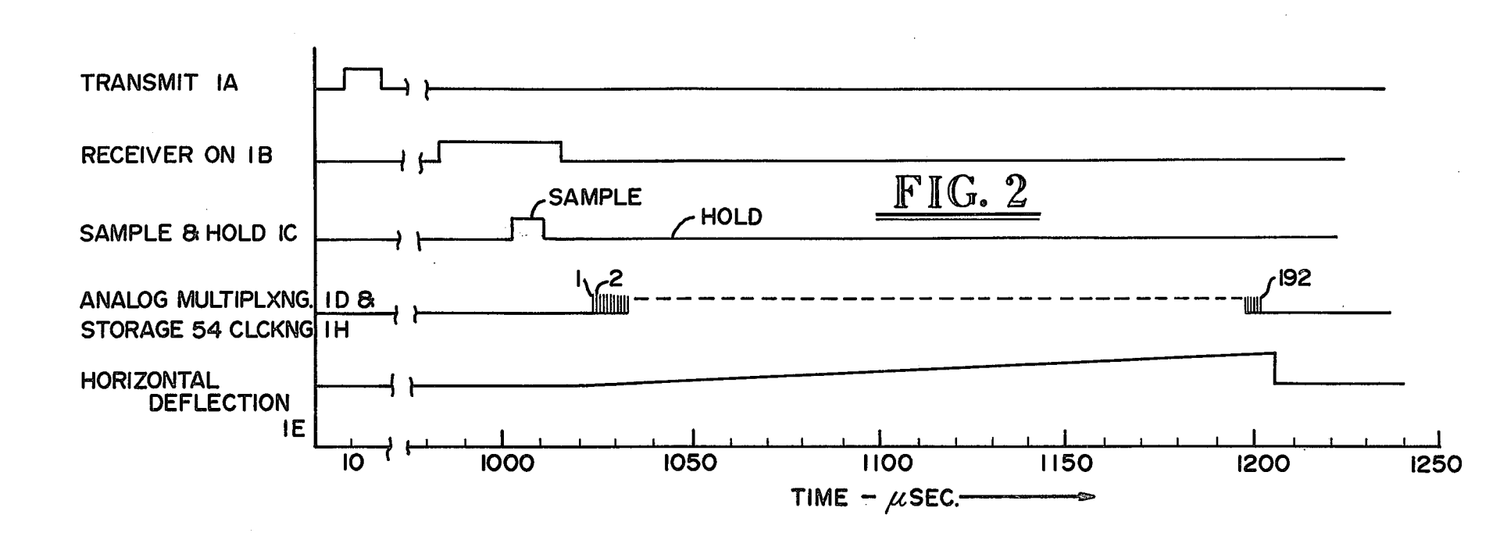
FIGS. 2 and 3 show waveform diagrams for signals developed at various locations within the system and relative timing thereof.
Figure 3:
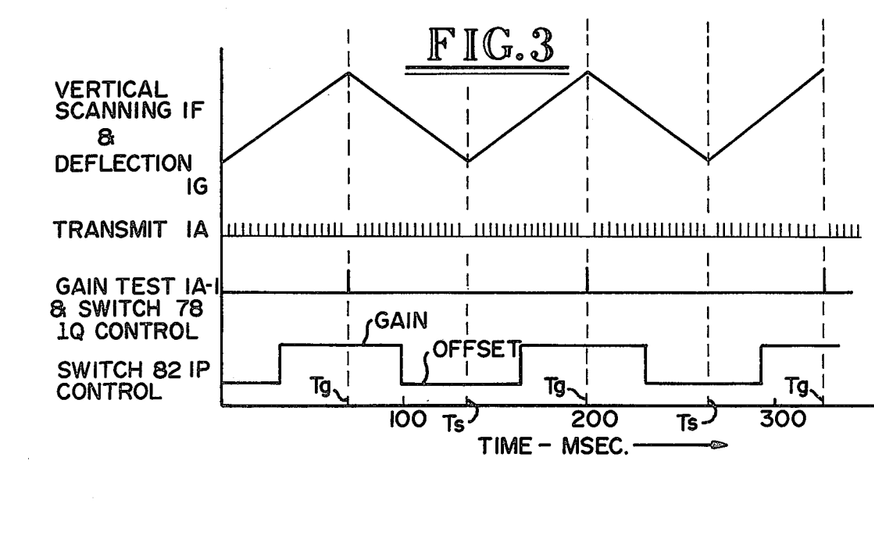

A brief description of the operation of the acoustic camera system, without error compensation, with reference to the timing diagrams of FIGS. 2 and 3, now will be made. The transmitter 40 is energized by recurrent pulses 1A, and the resultant ultrasonic wavefield travels through the object 12 and is focused by the lens 28 on the receiving array, whereupon electrical signals in response to the amplitude of the impinging acoustic wave image are produced thereat. The receivers 36 are turned on during pulse period 1B and, after receiver operation stabilizes, a sample signal 1C is applied to all of the sample and hold circuits 38 for the simultaneous sampling of the receiver outputs during the presence of the acoustic signals at the receiving array. Subsequently, information stored in the sample and hold circuits is sequentially read out by scanning operation of the analog multiplexer 44, which is sequentially stepped under control of pulses 1D. The composite video signal passes through the error correcting means 8 of this invention and is applied to the control grid of the cathode ray tube. During the multiplexing operation a horizontal deflection ramp signal 1E is applied to the cathode ray tube to sweep the electron beam across the face of the tube.

Synchronous vertical scanning control signal 1F and vertical deflection control signal 1G (FIG. 3) serve to sweep the receiver array 30 up and down in synchronism with the vertical deflection of the cathode ray tube beam. In practice many transmitting pulses 1A, say 400 pulses, may be produced for each cycle of operation of the vertical scanning and deflection signals, but for clarity of illustration fewer transmit pulses are shown in FIG. 3. Also, it will be noted that gaps in the generation of transmitting pulses 1A are provided at the ends of the vertical scan and deflection signals 1F and 1G, and it is during such periods that error sampling, or measuring, and updating of the error correcting means take place. Obviously, without automatic error compensation no such gaps in the operation are included.

In the illustrated acoustic camera system employing many channels of signal processing, the channels must all have identical operating characteristics such that the outputs therefrom are identical with identical input signals. In practice it is substantially impossible to adjust the individual channels for identical operation, and even if such adjustments were possible, drift during operation would vary from channel to channel, again upsetting the channel balance. With the present invention automatic compensation for the different operating characteristics is provided, which compensation may be performed periodically to minimize errors. Differences in channel outputs can be attributable to many causes including, for example, different transducer and receiver channel noise figures, gain, linearity and offset errors, and correction for one or more of such errors is contemplated.

Figure 4:
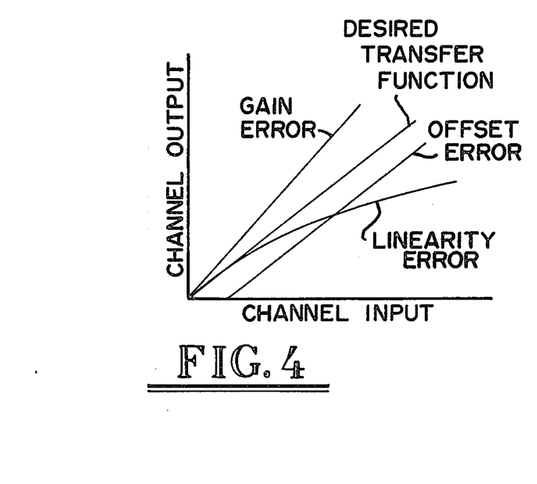
FIG. 4 is a graph showing the relationship between channel input and output signals for a channel having a desired transfer function and for channels with different operating errors.

As noted above, operation of the receiver amplifiers in either linear or nonlinear (e.g., logarithmic) modes is contemplated, and the novel error correction method and system of this invention are applicable in either case. For purposes of description linear channel operation is assumed, and in FIG. 4, to which reference now is made, the channel operating characteristic showing acoustic input to a receiver transducer element 32 versus analog output from the analog multiplexer 44 is shown for a linearly operated channel. For purposes of illustration the desired transfer function is shown as a straight line of constant slope passing through the zero of the input axis. As shown, with offset error the transfer function fails to pass through the origin, with gain error the transfer function passes through the origin but has a different slope, and with linearity error the transfer function deviates from a straight line. In the FIG. 1 arrangement, for purposes of illustration, any offset errors are compensated for by adding a constant signal of proper magnitude and sense to the channel outputs to shift the channel transfer function for passage thereof through the zero of the input axis.

As seen in FIG. 1, the composite video signal from the analog multiplexer 44, which is subject to the individual channel offset errors, is supplied to the amplifier 46 through an adder 50 and switch 52 included in the error correcting means 8. Offset error compensation signals for each information channel (1 through 192 in the illustrated system) are contained in an offset error compensation storage unit 54. Storage in either digital of analog form is contemplated. For purposes of illustration digital storage means are shown which may comprise, for example, a plurality of shift registers equal in number to the number of bits included in the individual error compensation signals to be stored. For example, if a five bit error correction signal is to be stored, then the storage unit may include five shift registers each having a capacity equal to the number of information channels (192 in the present example). The storage unit registers are clocked in synchronism with operation of the analog multiplexer 44 under control of clock signals from the timing and control unit 42 over line 1h, and the stored offset error compensation signals are fed through a digital to analog (D/A) converter 56 to the adder circuit 50, where the compensation signals are added to the corresponding channel signals to compensate for offset errors therein. In FIG. 2 the same control signals 1D and 1H are shown for synchronous operation of the analog multiplexer 44 and shift registers 54. With each shift of the registers the signals at the outputs thereof are returned to the register inputs through an adder 55. In the operating mode, during which the composite video signal is supplied to the cathode ray tube 16, the error compensating signals are returned unaltered to the input of the shift registers 54 through the adder 55 simply by operating the adder with zero signal inputs to the second adder input from a temporary storage unit 64 through a switch 58, by maintaining the switch in the open condition to inhibit passage of signals therethrough from the storage unit 64. It will be seen, then, that the illustrated storage unit 54 simply functions as a circulating storage device containing offset error compensation information which may be updated through use of adder 55.

Figure 5:
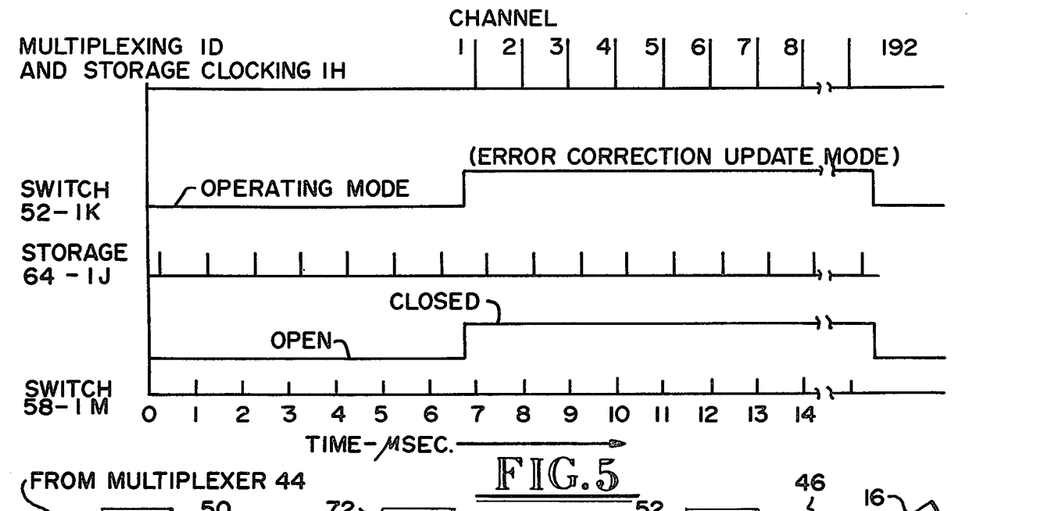
FIG. 5 is a waveform diagram similar to that of FIGS. 2 and 3 but on a shorter time scale.

Preferably, but not necessarily, offset errors in the corrected channel signal outputs are automatically sensed and the error compensation signals contained in storage unit 54 are periodically updated accordingly to prevent the accumulation of offset error drift in the channel outputs. In order not to interfere with the visual display at tube 16, error sensing and storage resetting are performed at the ends of the receiver array scanning and vertical deflection of the cathode ray tube beam. In the embodiment of FIG. 1 error sensing is accomplished by periodically comparing the 192 corrected channel outputs from the adder circuit 50 with a standard source to detect variations in the outputs from the standard. To this end a comparator circuit 60 is provided having as one input the composite signal from adder 50, when switch 52 is actuated to the broken line position, and having as a second input the standard signal from standard signal source 62. If the receiving channels are intended for operation with no d.c. offset, then a zero (0) standard signal source is used, e.g., a zero voltage source. Under such conditions, with no acoustic input signal to the receiver transducers 32, the channel outputs from the multiplexer 44 also should be at zero d.c. level. If any channel output from the adder 50 is not zero, an output is obtained from the comparator 60, which output is supplied to the temporary storage unit 64 and stored therein upon occurrence of a clock signal 1J (FIG. 5). With the switch 58 now closed, the stored error signal from temporary storage unit 64 is applied as an input to the adder 55. Consequently, when the shift registers of storage unit 54 subsequently are clocked by pulse 1H, the information returned to the shift register inputs is updated by an amount equal to that supplied to the adder from temporary storage unit 64. This updating of offset error compensation information contained in storage unit 54 is repeated for each channel (1 through 192), at the end of which sequence the switch 58 is reopened and the switch 52 is returned for operation in the normal operating mode described above.

As noted above, either analog or digital operation of the error compensation means 8 is contemplated. Also, updating of the error compensation storage unit 54 may be effected in the full amount of the error signal from the comparator 60, or only partially, dependent upon the sense of the error signal but not the magnitude thereof. FIG. 1 of the drawings illustrates an arrangement wherein the offset error compensation information is changed a predetermined, incremental amount dependent upon the sense of the comparator 60 output, independently of the magnitude thereof. As a result, operation of the system through several frames of video output may be required for proper error compensation. This preferred operating mode is readily adapted to digitally operating circuitry. For example, the temporary storage unit 64 simply may comprise a single bit storage device, such as a flip-flop or other bistable device, responsive to the sense but not magnitude of the error signal from the comparator. In such an arrangement, wherein only a single bit of information is supplied to the adder from the temporary storage, the adder simply may comprise an up-down, or reversible, counter for increasing or decreasing by one bit the information supplied thereto from the storage unit 64. It will be apparent that with such an arrangement large error compensation is incrementally effected in one direction over a number of operating frames. When substantially the desired error compensation signal is contained in storage unit 54, alternate up and down incremental changes about the desired operating point are produced during successive updating opertions.

Figure 6:
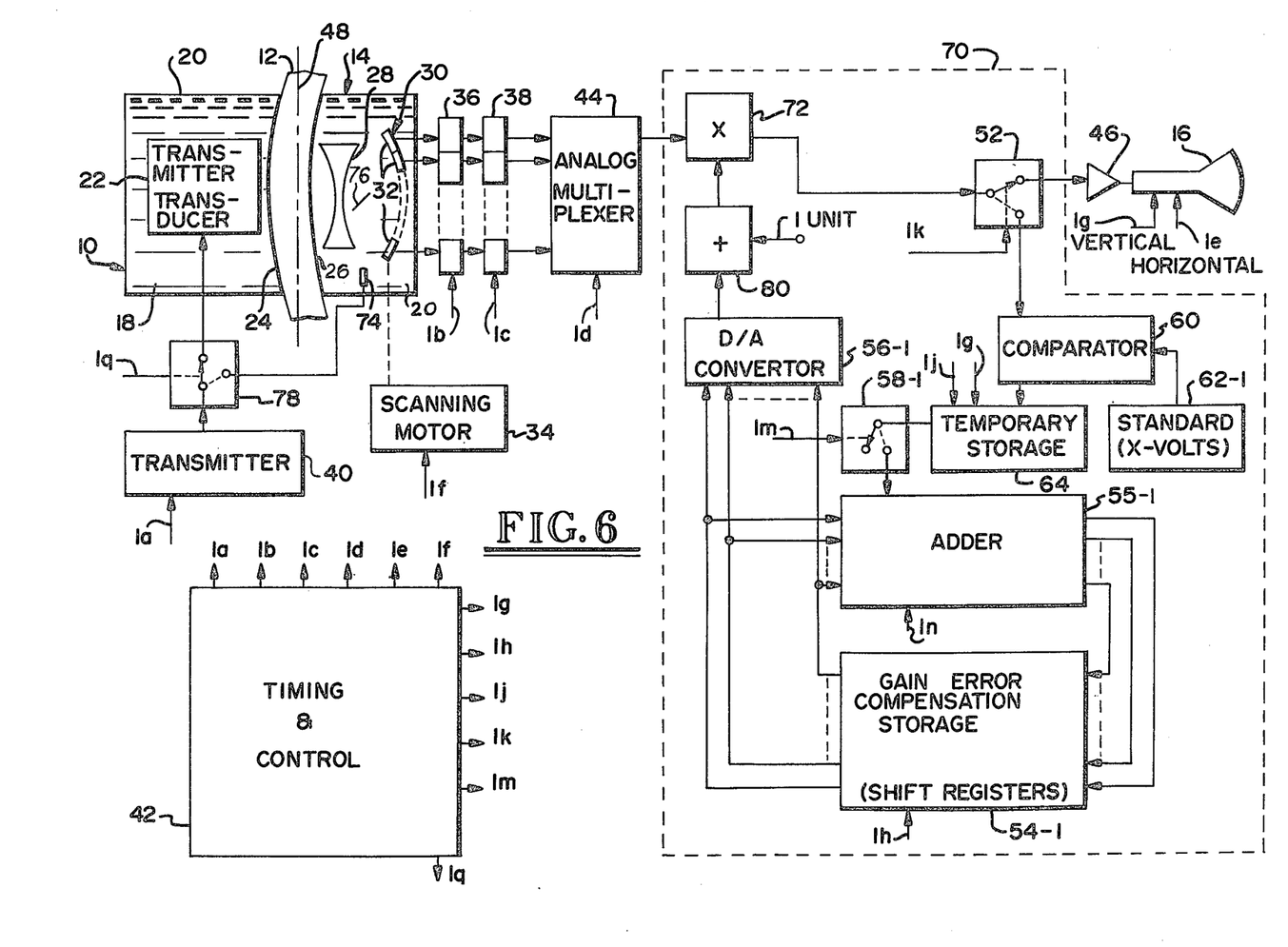
FIG. 6 is a block diagram of a modified embodiment of the invention similar to that of FIG. 1 but showing gain error compensation.

The invention is not limited to offset compensation, or correction, of the individual information channels. In FIG. 6, to which reference now is made, gain error compensating means 70 are shown for correction of errors in the slope of the channel functions. To detect channel gain errors an acoustic wave channel transfer generated which is coupled to the receiving array 30 for subjecting the individual transducer elements to identical field pressures. If the channels have identical operating characteristics, a constant level signal is obtained from the analog multiplexer 44 upon subsequent scanning of the sample and hold circuits by the analog multiplexer. Variations in the gains, however, result in variations in the channel outputs which are detected and used in the production of gain error compensation signals stored and supplied in synchronism with the channel outputs during subsequent operating cycles to a multiplier circuit 72 included in the compensation circuit 70. By multiplying the individual channel outputs in the proper amounts the slope of the individual channel transfer functions is altered to correct for gain errors. For purposes of this description the absence of other channel operating characteristic errors is assumed.

The transmitting transducer 22 may be used to generate the necessary ultrasonic waves for subjecting the receiver transducer elements to equal acoustic field pressures by directly coupling the receiver unit 14 to the transmitting unit 10 without an object 12 therebetween. In the arrangement shown in FIG. 6 a separate point source transmitting transducer 74 is located within the receiving unit 14 for uniform acoustic exposure of the receiver elements without the necessity of removing the subject 12 from the system. A mostly transmissive, slightly reflective element 76 is included in the receiving unit between the receiving array 30 and acoustic lens 28 comprising, for example, a thin plastic member or membrane. The partially reflective member is positioned for reflection of a portion of the wavefield generated by the transducer 74 onto the array 30 for uniform insonification of the receiver transducer elements 32. The transducer 74 may be energized by periodically switching the output from the transmitter 40 thereto through switch 78 which is controlled by signal 1Q supplied to the switch from the timing and control circuit 42 over circuit 1g. In FIG. 3 the transducer 74 test signal 1A-1 and switch 78 control signal 1Q are shown generated periodically at times Tg at opposite half cycles from which offset error correction takes place at times Ts. Obviously, the offset Ts and gain Tg sensing times could occur in adjacent operating cycles at one end of the vertical scan, if desired.

In FIG. 6 correction for gain error only is shown for simplicity. Gain error compensation signals are contained in storage unit 54-1, which unit may be of the same type as storage unit 54 and clocked by the same signal 1H supplied thereto over line 1h. The gain error compensation signals are fed through a D/A converter 56-1 and adder circuit 80 to the multiplier circuit 72. A unit signal is supplied as a second input to the adder to normalize the gain error compensation signal for use as a multiplier input. Obviously, the shift registers of storage unit 54-1 could be operated with such normalization signal in storage, or the standard 62-1 could include the same. The channel output signals from analog multiplexer 44 are multiplied by the gain error compensation signals to alter the slope of the channel transfer function, when necessary, for the desired slope. As in the offset error correcting arrangement shown in FIG. 1, the gain error compensation signals are returned unaltered through adder 55-1 to the storage input during the operating mode.

Periodic updating of the gain error compensation signals is performed in a manner similar to that employed for updating stored offset error compensation signals, except that an acoustic test signal of a magnitude other than zero is supplied to receiver transducer elements 32 as by use of transducer 74, and the resultant composite video signal supplied to the comparator 60 through switch 52 is compared with an appropriate standard 62-1 which may be at the same level as the desired channel output. For purposes of illustration a standard X volt signal is shown and, if the channel output deviates therefrom, an output is obtained from the comparator 60 which is temporarily stored and subsequently supplied through switch 58-1 to adder 55-1 to be added to the gain error compensation signal being returned therethrough to storage 54-1, all in a similar manner to that shown in FIG. 1 for offset error compensation.

Figure 7:
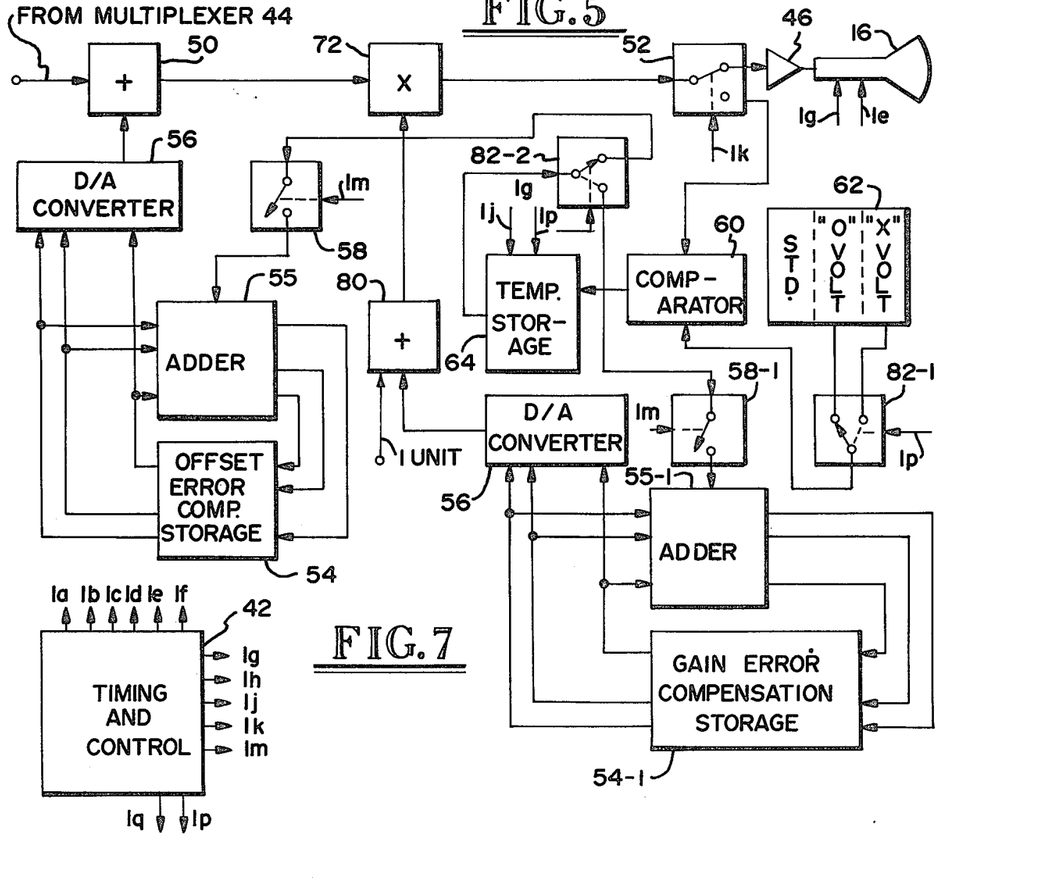
FIG. 7 is a block diagram showing both offset and gain error compensation of multichannel outputs.

With the error compensating method and means of this invention compensation for more than one type of channel transfer function error is readily accomplished. For example, in the arrangement of FIG. 7, offset and gain errors in the channel outputs are compensated by feeding the multiplexer 44 output through adder and multiplier circuit 50 and 72, respectively, which are simultaneously supplied with the required offset and gain error compensation signals from storage units 54 and 54-1 operated in synchronism with the analog multiplexer. With this arrangement updating of the contents of the storage units 54 and 54-1 is effected during alternate updating modes. During offset error compensation updating switch sections 82-1 and 82-2 are actuated to the illustrated full line positions for connection of the 0 volt standard 62 to the comparator 60 and for connection of the output from the temporary storage unit 64 to the adder 55 through closed switch 58, respectively. Conversely, during gain error compensation updating the switch sections 82-1 and 82-2 are actuated to the broken line positions for connection of the X volt standard 62-1 to the comparator 60 and the output from the temporary storage unit 64 to the adder 55-1 through closed switch 58-1, respectively. A switch control signal 1P (FIG. 3) from timing and control unit 42 is connected to the switch sections over circuit 1p for proper control of switch sections 82-1 and 82-2. Updating of the contents of storage units 54 and 54-1 in other respects is the same as that shown in FIGS. 1 and 6 described above and requires no additional description.

In the illustrated arrangements it is seen that gain error measurements are dependent both upon gain and offset errors (in addition to linearity errors, which for present purposes are assumed not be be present). Consequently, changes in offset error corrections during updating subsequently will result in changes in the measured gain error. By incrementally changing the storage contents, as described, a stable system results which operates about the correct, or desired, transfer functions without widely varying swings therein.

The invention having been described in detail in accordance with the requirements of the Patent Statutes, other changes and modifications will suggest themselves to those skilled in this art. For example, for linearity error compensation a plurality of correction signals for each channel may be stored and supplied to the multiplier circuit (such as multiplier circuit 72 of FIG. 6) according to the level of the operating signal. Obviously, different level test signals applied over a series of operations would be required to update the linearity error correction storage means.

Also, it readily will be apparent that the multichannel system to which the error compensation method is applied is not limited to acoustic camera systems, there being many other systems, e.g., X-ray types, employing a plurality of like signal handling channels. Also, the channels involved may be of a wide variety of types and are not limited to the illustrated arrangement of transducers, receivers, sample and hold circuits, and analog multiplexer. The compensating method and means of this invention are usable in substantially any multichannel arrangement which is subject to offset, gain, or like operating errors. Addditionally, instead of automatic periodic updating of stored error compensating signals, it will be apparent that manual control thereof is possible for updating at any desired times. For example, test signals could be applied daily, after system warm up, for sensing variations in channel operations and updating the stored error compensating signals. It is intended that these and other such modifications which fall within the spirit and scope of the invention will be covered by the appended claims.

What is claimed is:

1. In an arrangement of the type which includes a plurality of substantially identical signal processing channels having input circuits to which input signals are applied and which signal processing channels are designed to provide identical output signals with identical input signals, error compensating means for compensating for variations in operating characteristics of said signal processing channels to substantially equalize selected operating characteristics of the channels, said error compensating means comprising:

error compensation signal storage means for storage of error compensation signals for each channel;

means for combining the outputs from said signal processing channels with associated error compensation signals in storage to compensate for variations in certain signal processing channel operating characteristics, means for supplying the signal processing channels with a test signal which is substantially the same for each channel;

signal standard means related to said test signal, and means for sensing variations of test signal outputs from sad combining means from said related signal standard means and updating said stored error compensation signals accordingly.

2. In an arrangement as defined in claim 1, including means for recurrently updating the stored error compensation signals by recurrent operation of said test signal and signal standard means.

3. In an arrangement as defined in claim 2, wherein said signal processing channels are included in an ultrasonic imaging apparatus which includes a transducer array having individual transducer elements responsive to instantaneous acoustic field pressure, said means for supplying the signal processing channels with a test signal comprising means for generating an ultrasonic wave for simultaneously uniformly insonifying said transducer elements.

4. In an arrangement as defined in claim 1, wherein said means for sensing test signal variations comprises:

a comparator having as one input the error compensated test signals from said combining means and as another input an output from said signal standard means; and means for recurrently switching the output from the combining means to said comparator in the presence of test signal outputs from said combining means.

5. In a method of compensating for variations in certain operating characteristics of a plurality of substantially identical information handling channels designed to provide identical output signals with identical input signals applied thereto, said channels being included in an information handling system:

combining the individual channel outputs with associated individual error compensating signals from error compensation storage means to compensate for said variations;

simultaneously recurrently supplying said information handling channels with a test signal which is substantially equal for each channel input;

sensing variations in the error compensated test signal from a signal standard related to said test signal; and utilizing said variations to recurrently update the error compensation signals in said error compensation storage means accordingly.

6. In a method of compensating as defined in claim 5, wherein said channel outputs are combined with error compensating signals by adding to compensate for offset errors in the information handling channels.

7. In a method of compensating as defined in claim 5, wherein said channel outputs are multiplied by said error compensating signals in combining the same to compensate for gain errors in the information handling channels.

8. Error compensating means to compensate for variations in certain operating characteristics of a plurality of information handling channels which are multiplexed to produce a composite signal, said error compensating means comprising:

error compensating signal storage means for storage of error compensating signals for each information handling channel;

means for combining the error compensating signals from the storage means with the multiplexed channel signals to compensate for variations in certain operating characteristics of the information handling channels;

means for supplying the information handling channels with a test signal;

means for sensing variations in the compensated multiplexed test signals from a standard related to the test signal; and means employing the outputs from said sensing means for updating the stored error compensating signals contained in storage.

9. The error compensating means as defined in claim 8, wherein said means for combining the error compensating and channel signals comprises an adder circuit and said test signal inputs are zero for compensation of offset errors in the information handling channels.

10. The error compensating means as defined in claim 8, wherein said means for combining the error compensating and channel signals comprises a multiplier circuit and said test signal inputs are nonzero for compensation of gain errors in the information handling channels.

11. The error compensating means as defined in claim 8, wherein said means for combining the error compensating and channel signals comprise series connected adder and multiplier circuits and wherein said test signal inputs are alternately zero and nonzero, respectively, for compensation of offset and gain errors in the information handling channels.

12. The error compensating means as defined in claim 8, wherein said information handling channels include a plurality of transducer elements responsive to an energy field received from an object for converting the same to electrical signals and a plurality of electrical signal storage means for storing signals from individual receiver transducer elements, the outputs from which signal storage means are multiplexed to produce said composite signal.

13. The error compensating means as defined in claim 12, wherein said test signal input comprises no energy field at the transducer elements and said means for combining the error compensating and multiplexed channel signals comprises an adder circuit for compensation of offset errors.

14. The error compensating means as defined in claim 12, wherein said transducer elements are of the ultrasonic type and said test signal input comprises an ultrasonic wave for uniformly insonifying said ultrasonic transducer elements, and wherein said means for combining the error compensating and multiplexed channel signals comprises a multiplier circuit for compensation of gain errors.

15. The error compensating means as defined in claim 8, wherein said error compensating signal storage means comprise shift registers.

* * * * *